US00PP25497P3

(12) United States Plant Patent
Olesen

(10) Patent No.: US PP25,497 P3
(45) Date of Patent: May 5, 2015

(54) MINIATURE ROSE PLANT NAMED 'POULPAH066'

(50) Latin Name: ***Rosa* hybrid**
Varietal Denomination: Poulpah066

(71) Applicant: Mogens Nyegaard Olesen, Fredensborg (DK)

(72) Inventor: Mogens Nyegaard Olesen, Fredensborg (DK)

(73) Assignee: Poulsen Roser A/S, Fredensborg (DK)

( * ) Notice: Subject to any disclaimer, the term of this patent is extended or adjusted under 35 U.S.C. 154(b) by 83 days.

(21) Appl. No.: 13/986,916

(22) Filed: Jun. 14, 2013

(65) Prior Publication Data

US 2014/0373219 P1 Dec. 18, 2014

(51) Int. Cl.
*A01H 5/00* (2006.01)

(52) U.S. Cl.
USPC ..... Plt./122

(58) Field of Classification Search
USPC ..... Plt./122, 129
See application file for complete search history.

*Primary Examiner* — Kent L Bell

(57) ABSTRACT

A new miniature rose plant that has abundant, red flowers and attractive foliage. The variety successfully propagates from softwood cuttings and is suitable for year-round production in commercial glasshouses. This new and distinct variety has shown to be uniform and stable in the resulting generations from asexual propagation.

1 Drawing Sheet

Botanical designation: *Rosa* hybrid.
Variety denomination: 'Poulpah066'.

SUMMARY OF THE INVENTION

The present invention constitutes a new and distinct variety of miniature rose plant which originated from a controlled crossing between the female seed parent, an unnamed seedling, and the male pollen parent, also an unnamed seedling.

The two parents were crossed during the summer of 2007 and the resulting seeds were planted in a controlled environment in Fredensborg, Denmark. The new variety, named 'Poulpah066', originated as a single seedling from the stated cross.

The new variety may be distinguished from its male pollen parent and female seed parent primarily by flower coloration and growth habit.

The objective of the hybridization of this rose variety for commercial culture was to create a new and distinct variety with unique qualities, such as:

1. Uniform and abundant red flowers;
2. Vigorous and compact growth;
3. Year-round flowering under glasshouse conditions;
4. Suitability for production from softwood cuttings in pots;
5. Durable flowers and foliage which make a variety suitable for distribution in the floral industry.

This combination of qualities is not present in previously available commercial cultivars of this type, known to the inventor, and distinguish 'Poulpah066' from all other varieties of which we are aware.

As part of the rose development program, Mogens N. Olesen germinated the seeds from the aforementioned hybridization and conducted evaluations on the resulting seedlings in a controlled environment in Fredensborg, Denmark. 'Poulpah066' was selected by the inventor as a single plant from the progeny of the hybridization in 2007.

Asexual reproduction of 'Poulpah066' by cuttings was first done by Mogens N. Olesen in the nursery in Fredensborg, Denmark in 2008. This initial and other subsequent propagations conducted in controlled environments have demonstrated that the characteristics of 'Poulpah066' are true to type and are transmitted from one generation to the next.

DESCRIPTION OF THE DRAWING

The accompanying color illustration shows as true as is reasonably possible to obtain in color photographs of this type, the typical characteristics of the buds, flowers, leaves, and stems, of 'Poulpah066'. Specifically illustrated in the drawing are flowers at various stages of development, flower in parts, leaves, and stems.

DETAILED DESCRIPTION OF THE VARIETY

The following is a description of 'Poulpah066', as observed in its growth in an outdoor container nursery in Oregon. Observed plants are 9 months of age and were cultivated in 1 gallon containers. Color references are made using The Royal Horticultural Society (London, England) Colour Chart, 2001, except where common terms of color are used.

For a comparison, several physical characteristics of the rose variety 'Poulrouge', U.S. Plant Pat. No. 9,687 are compared to 'Poulpah066' in Chart 1.

CHART 1

| | 'Poulpah066' | 'Poulrouge' |
|---|---|---|
| Petalage: | 40 | 30 to 35 |
| Flower Diameter: | 65 mm | 1.5 inches (38 mm) |
| Upper petal surface coloration: | Red Group 53B | Red Group 40B |

FLOWER AND FLOWER BUD

Blooming habit: Continuous.

Flower bud:

*Size*.—Upon opening, 21 mm in length from base of receptacle to end of bud. 14 mm in diameter.

*Bud form*.—Urceolate.

*Bud color*.—As sepals divide, petals are Red Group 53B to 53C.

*Sepals*.—Upper Surface: Color: Green Group 138B and 138A with anthocyanin the color of Greyed-Red Group 178A. Texture: Smooth, weakly pubescent. Lower Surface: Color: Yellow Green Group 144A with intonations of Greyed-Purple 183B. Texture: Smooth. Shape: Apex: Cirrhose. Base: Flat at union with receptacle. Margins: Margins have weak foliaceous appendages on three of the five sepals. Size: 21 mm long by 11 mm wide.

*Receptacle*.—Surface Texture: Smooth. Shape: Campanulate. Size: 5 mm tall and 7 mm wide. Color: Yellow Green Group 144A, and Greyed-Purple Group 183B.

*Pedicel*.—Surface: Somewhat rough with stipitate glands. Length: 22 mm on average. Diameter: Generally 3 mm. Color: Yellow-Green Group 144A with Greyed-Red Group 178B. Strength: Strong.

*Borne*.—Singly and clusters of 3.

Flower bloom:

*Fragrance*.—Light floral fruity scent.

*Duration*.—As a pot plant, flowers last up to 25 days.

*Size*.—Flower diameter is 65 mm when open. Flower depth is 22 mm.

*Form*.—General shape is a hybrid tea initially, and opens into a rosette with many overlapping petals.

*Shape of flower, side view*.—The upper portion is flat. The lower portion is a concave.

Petalage: Under normal conditions, flowers have 40 petals total, 3 of which are petaloids.

Color:

*General tonality*.—On open flower Red Group 53B.

*Upon opening, petals*.—Inner and outermost petals are Red Group 53B on the upper surface, underneath Red Group 53A, shaded lightly with Red-Purple Group 58B. The upper surface has a petal spot Yellow Group 8B. Underneath petal spot is White Group 155A.

*After opening, petals*.—Inner and outermost petals are Red Group 53B on the upper surface, underneath Red Group 53A, shaded lightly with Red-Purple Group 58B. The upper surface has a petal spot Yellow Group 8B. Underneath petal spot is White Group 155A.

Petals:

*Petal reflex*.—Medium.

*Margin*.—Entire. Medium undulations.

*Shape*.—Generally broad and ovate. Apex shape: Rounded. Base shape: Broad.

*Size*.—45 mm (l) by 31 mm (w).

*Texture*.—Smooth.

*Thickness*.—Thick.

Petaloids:

*Quantity*.—3 on average.

*Shape*.—The apex is rounded and base is acute.

*Color*.—Red Group 53B on the upper surface, underneath Red Group 53A, shaded lightly with Red-Purple Group 58B. The upper surface has a petal spot Yellow Group 8B. Underneath petal spot is White Group 155A.

*Size*.—8 mm (1) by 5 mm (w).

Reproductive organs:

*Pollen*.—None Observed.

*Anthers*.—Size: 2 mm long. Color: Yellow Group 12D. Quantity: 60 on average.

*Filaments*.—Color: Yellow Group 12A and Orange-Red Group 30A. Length: About 4 mm.

*Pistils*.—Length: About 7 mm long. Quantity: 30 on average.

*Stigmas*.—Superior relative to the length of the filaments and the height of the anthers. Color: Greyed-Yellow Group 160C.

*Styles*.—Color: White Group 155B and Red Group 39B.

*Seed formation*.—Not observed.

PLANT

Plant growth: Upright. Plants are 20 cm in height, and 20 cm wide.

Stems:

*Color*.—Juvenile growth: Yellow-Green Group 144B. Mature growth: Yellow-Green Group 144A with Greyed-Red Group 178A.

*Length*.—Canes are 12 cm from the base of the plant to the flowering portion.

*Diameter*.—3 to 4 mm.

*Internodes*.—On mature canes, there is an average distance of 10 mm between nodes.

*Surface texture*.—Young and mature wood is smooth.

Prickles.—None observed.

Plant foliage:

*Compound leaf size*.—95 mm (l) by 65 mm (w).

*Quantity*.—5 to 6 leaves per 10 cm of stem.

*Color of juvenile foliage*.—Upper Leaf Surface: Yellow-Green Group 144A with margins Greyed-Red Group 178A. Lower Leaf Surface: Yellow-Green Group 146B.

*Color of mature foliage*.—Upper Leaf Surface: Yellow-Green Group 146A. Lower Leaf Surface: Yellow-Green Group 146B.

Plant leaves and leaflets:

*Stipules*.—Size: About 7 mm in length. Shape: Linear, slightly broad based with outward extending apecies. Margins: Finely serrated with few stipitate glands. Color: Yellow-Green Group 144A.

*Petiole*.—Length: 20 mm on average. Diameter: 1-2 mm. Upper surface: Yellow-Green Group 146A. Lower surface: Yellow-Green Group 144A.

*Rachis*.—Length: 35 mm on average. Diameter: About 2 mm. Upper surface: Yellow-Green Group 146A. Lower surface: Yellow-Green Group 144A. Small prickles.

*Leaflet*.—Number of leaflets: 5 on normal leaves in middle of the stem. Size: 40 mm in length by 32 mm wide. Margin: Serrate. General Shape: Orbicular. Apex Shape: Mucronate. Base Shape: Round. Texture: Smooth. Arrangement: Odd pinnate. Venation: Reticulate. Leaf Gloss: Glossy.

Cold hardiness: The variety is tolerant to USDA Cold Hardiness Zone 6.

Heat tolerance: The variety has been found to be suitable for climate conditions found in the American Horticulture Society heat zone 7.

The invention claimed is:

1. A new and distinct variety of rose plant of the miniature class named 'Poulpah066', substantially as illustrated and described herein, due to its abundant, red flowers, vigorous growth, compact habit, suitability for production from softwood cuttings in pots, and durable flowers and foliage that make the variety suitable for distribution in the floral industry.

* * * * *

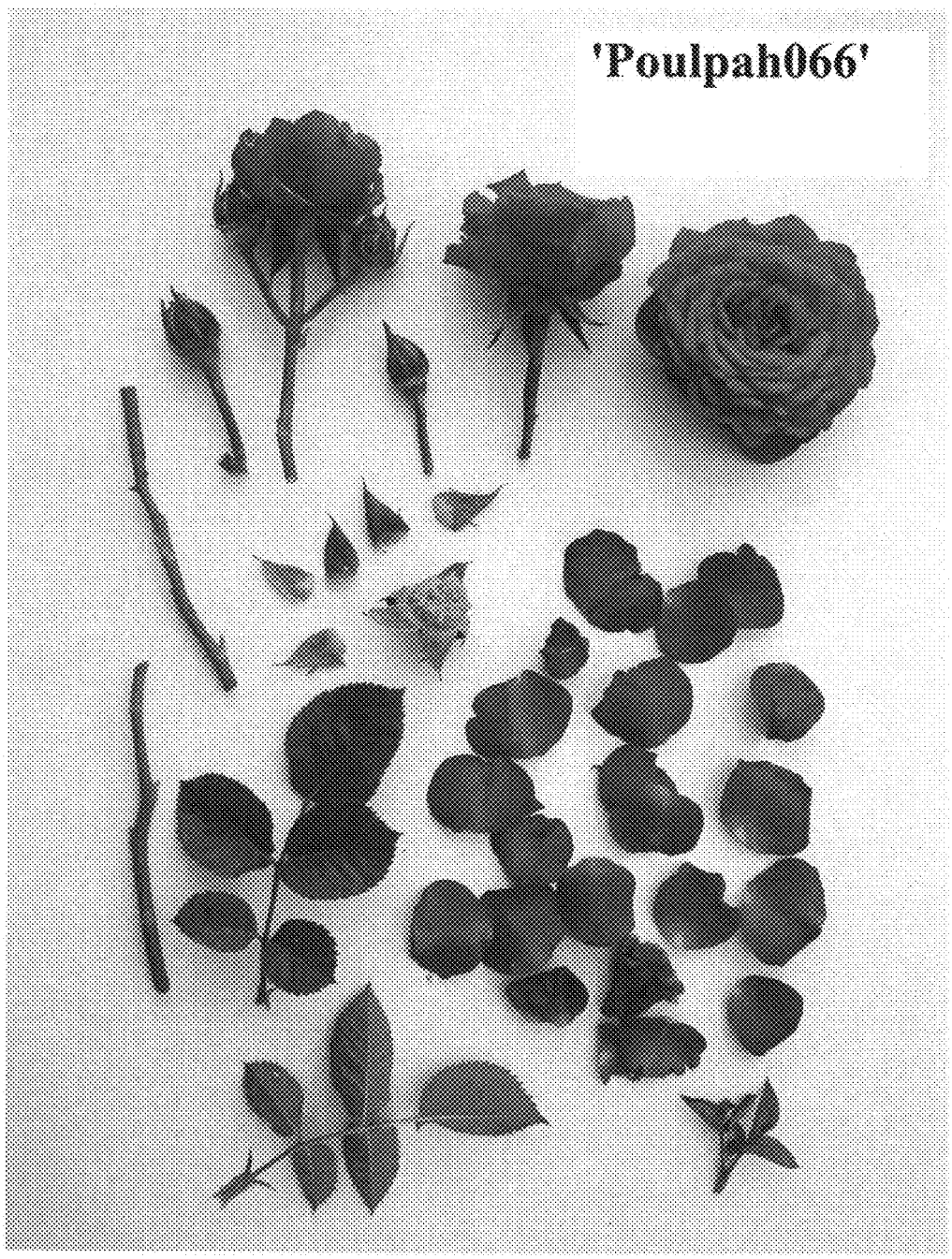
'Poulpah066'